(12) United States Patent
Herrera et al.

(10) Patent No.: US 8,094,031 B1
(45) Date of Patent: Jan. 10, 2012

(54) DEVICE AND METHOD FOR DETECTING LEAKS AND PROTECTING SURFACES FROM WATER DAMAGE DUE TO LEAKS

(76) Inventors: Mark Richard Herrera, Jackson, CA (US); Lisa Marie Herrera, Jackson, CA (US)

( * ) Notice: Subject to any disclaimer, the term of this patent is extended or adjusted under 35 U.S.C. 154(b) by 450 days.

(21) Appl. No.: 12/423,809

(22) Filed: Apr. 15, 2009

(51) Int. Cl.
*G08B 21/00* (2006.01)
(52) U.S. Cl. ........ 340/605; 340/606; 340/612; 340/616; 340/618; 340/573.6; 422/50; 422/551; 116/200; 116/204
(58) Field of Classification Search .................. 340/605, 340/606, 612, 616, 618, 573.6; 422/50, 551; 116/200, 204
See application file for complete search history.

(56) References Cited

U.S. PATENT DOCUMENTS

| | | | |
|---|---|---|---|
| 6,524,857 B1 * | 2/2003 | Perkins | 436/3 |
| 2004/0115818 A1 * | 6/2004 | Puri et al. | 436/3 |

* cited by examiner

*Primary Examiner* — Tai T Nguyen
(74) *Attorney, Agent, or Firm* — Michael D. Eisenberg

(57) ABSTRACT

An air freshening device is provided for detecting water leaks and protecting surfaces from water damage due to leaks. The device includes: a tray, configured for being placed upon a surface located under a water pipe; a removable and replaceable liner placed upon the tray, the liner comprising a material configured for releasing an air freshening substance into air, and for increasing the release rate of the substance upon contact with water. The increase of the release rate of the substance leads to an intensifying of the scent of the substance in air, and indicates the presence of a leak from the water pipe. The tray prevents water leaking from the water pipe from touching the surface.

18 Claims, 7 Drawing Sheets

DEVICE AND METHOD FOR DETECTING LEAKS AND PROTECTING SURFACES FROM WATER DAMAGE DUE TO LEAKS

TECHNICAL FIELD

The present invention relates to the detection of leaks, particularly, but not exclusively, to the detection of water leaks, and the protection of surfaces from water damage due to leaks.

BACKGROUND OF THE INVENTION

Water leaks are a common occurrence in households. An undetected leak may cause the accumulation of standing water on a surface. Standing water may cause an unpleasant smell, and may damage the surface on which the water is located.

Some of the causes for water leaks may lie in problems with dishwashers, air conditioners, faucets, washing machines, and water piping. Common surfaces that may be ruined by leaking water include bottom surfaces of cabinets located under sinks, such as kitchen sinks and bathroom sinks.

It may be therefore useful to have a device and a method for detecting water leaks and protecting surfaces from water damage, before the detecting is performed.

BRIEF SUMMARY OF EMBODIMENTS OF THE INVENTION

The present invention, in some embodiments thereof, relates to a device and method for detecting water leaks and for protecting surface from water damage caused by the leak.

An aspect of some embodiments of the present invention relates to an air freshening device for detecting water leaks and protecting surfaces from water damage due to leaks. The device includes: a tray, configured for being placed upon a surface located under a water pipe; a removable and replaceable liner placed upon the tray, the liner comprising a material configured for releasing an air freshening substance into air, and for increasing the release rate of the substance upon contact with water. The increase of the release rate of the substance leads to an intensifying of the scent of the substance in air, and indicates the presence of a leak from the water pipe. The tray prevents water leaking from the water pipe from touching the surface.

Optionally, the liner is flexible.

In a variant, the liner is at least partially enclosed in a rigid cartridge.

In another variant, the liner is available in different scents.

In a further variant, the material includes a water soluble barrier covering the substance and limiting the release of the substance, the water soluble barrier being configured for dissolving upon contact with water, thereby causing an increase of the rate at which the substance is released into air.

Optionally, the water soluble barrier comprises at least a water soluble polymer.

In yet a further variant, the above device further includes: a detector, configured for monitoring a density of the substance in air; and an alarm connected to the detector, and being configured for being activated by the detector, when the density of the substance increases above a predetermined density.

According to some embodiments of the present invention, the above device, further includes an item supporting member held by the tray above the liner, the member being configured for supporting at least one item, while allowing water to reach the liner.

Optionally, the item supporting member is one of: a perforated panel held by the tray above the material, the panel being configured for supporting at least one item, while allowing water to reach the material; and a grid of wires held by the tray above the material, the wire grid being configured for supporting at least one item, while allowing water to reach the material.

In a variant, the above device further includes walls along the perimeter of the tray, such that at least one of the walls comprises a gate configured for being opened and closed, thereby allowing the liner to be replaced, without the need to remove the tray from the surface.

In another variant, the tray is configured for being inserted into a cabinet located under a sink, and wherein the surface is the bottom surface of the cabinet.

In a further variant, a cabinet is provided, the cabinet including the above device, and being configured for being located under a sink.

Another aspect of some embodiments of the present invention relate to a device for detecting water leaks and protecting surfaces from water damage due to leaks. The device includes: a tray, configured for being placed upon a surface located under a water pipe; a material placed upon the tray, the material being configured for releasing a substance into air, upon contact with water. The release of the substance indicates the presence of a leak from the water pipe, and the tray prevents water leaking from the water pipe from touching the surface.

Optionally, the material is included in one of: a liner; a liquid configured for being sprayed upon the tray and, drying to form a film upon the tray; and a plurality of pellets or granules.

A further aspect of some of the embodiments of the present invention relates to method for freshening air, detecting water leaks, and protecting surfaces from water damage. The method includes: placing a tray a upon a surface located under a water pipe, the tray being configured for preventing water leaking from the water pipe from touching the surface; providing a removable and replaceable liner placed onto the tray, the liner comprising a material being configured for releasing an air freshening substance into air, and for increasing a release rate of the substance upon contact with water; releasing the air freshening substance into air; contacting the material with water leaking from the water pipe; increasing the release rate of the substance the substance into air; and detecting an increased quantity of the substance in the air.

In a variant, the above method further includes: replacing the liner, when needed; and checking the tray for the presence of water.

In another variant, the replacing comprises replacing the liner with a liner configured for releasing a substance with a different scent.

In a further variant, the material comprises a water soluble barrier covering the and limiting the release of the substance in air, the water soluble barrier being configured for dissolving upon contact with water, thereby causing an increase of the rate at which the substance is released into air.

Optionally, the detecting is performed through a user's sense of smell.

In yet a further variant, the detecting includes: using a detector for monitoring a density of the substance in air; and activating an alarm, if the density of the substance in air increases above a predetermined density.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

Figure 1A:
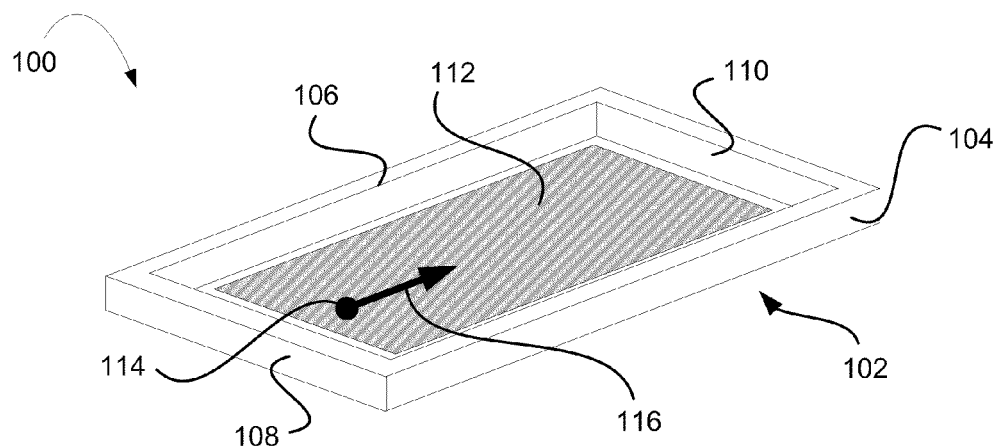
FIGS. 1a-1b are schematic drawings representing a device for detecting leaks and protecting surface from leaks, including a tray upon which is placed a material configured for releasing a detectable substance, upon contact with water, according to some embodiments of the present invention.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

The present invention relates to the detection of leaks, particularly, but not exclusively, to the detection of water leaks, and the protection of surfaces from water damage due to leaks.

An aspect of some embodiments of the present invention relates to an air freshening device for detecting water leaks and protecting surfaces from water damage due to leaks. The device includes a tray and a liner including an air freshening material, designed for releasing a scented substance into the air, and for increase a release rate of the substance when the material comes into contact with water. The tray is placed upon a surface under a water pipe, and is designed for catching water leaking form the pipe, thereby preventing contact between the water and the surface. The presence of the substance in increased quantity in the air is detected, and indicated a water leak.

According to some embodiments of the present invention, the material includes a water soluble barrier, such as a water soluble polymer, which covers the substance. The water soluble barrier covers the scented substance and limits a rate of release of the substance. Once water comes into contact with the barrier and dissolves the barrier, the substance is released into air at an increased rate. The substance may include a volatile substance, such as naphthalene, or an aerosol which includes one or more essential oils.

According to other embodiments of the present invention, the material 112 is designed to react with water, and the released substance is the product of the chemical reaction. The released substance may be, for example a gas, an aerosol or a volatile substance.

Optionally, the substance includes an odorant and may be detected by a user, for example through the user's sense of smell. Alternatively, the substance is designed to be detected by a detector, which is designed to activate an alarm, once a density larger than a predetermined density of the substance in the air is measured by the detector.

The scented substance is characterized by a pleasant odor designed for covering and/or absorbing malodors. The device is therefore further designed, for preventing the area below the water pipe to smell unpleasantly. This configuration may be particularly, but not exclusively, applicable to closed spaces, such as cabinets.

In a variant, the device includes an item supporting member designed for supporting one or more items. Such a device may be used to cover the bottom of a cabinet located under a sink. The item supporting member is designed for being held by the tray above the liner. The item supporting member is designed to support one or more items, while allowing water from a leak to reach the liner. Exemplary item supporting members include a perforated panel, or a wire grid.

According to some embodiments of the present invention, the tray is designed for allowing easy access to the liner, for removing and/or replacing of the liner, without moving the whole device. Such a design may be useful for a device covering the bottom surface of a cabinet, since removing the liner alone may not require a user to remove one or more items placed on the item supporting member of the device. Optionally, access is granted through an openable and closable gate included in at least one of the walls of the tray. Optionally, the tray is characterized by one low wall, above which a space is provided for easy access of the material.

Another aspect of the present invention relates to a method for freshening air, detecting water leaks, and protecting surfaces from water damage due to leaks.

Figure 1B:
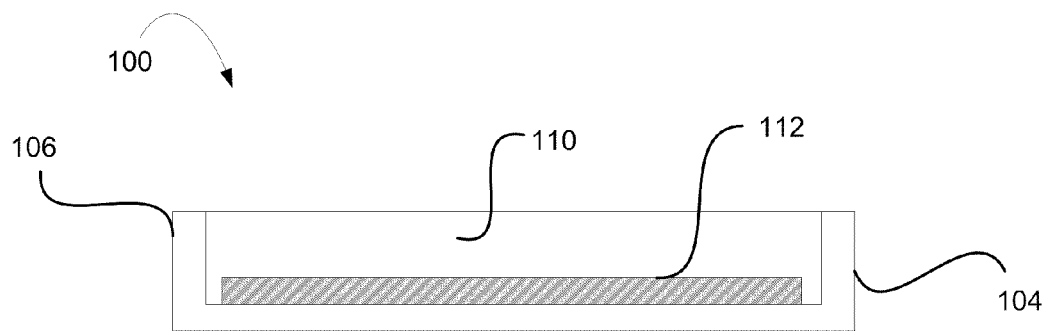

Referring now to the figures, FIGS. 1a-1b are schematic drawings representing a device 100 for detecting leaks and protecting surface from leaks. The device 100 includes a tray upon which a material is placed, the material being configured for releasing a detectable substance upon contact with water, according to some embodiments of the present invention. The substance may be a scented substance, designed for freshening air.

FIG. 1a shows a perspective view of the device 100. The device 100 includes a tray 102, characterized by a front wall 104, a back wall 106, a left wall 108, and a right wall 110. On the surface of the tray 102, a material 112 is placed. According to some embodiments of the present invention, the material 112 is designed to release a scented substance into air, and for increasing the release rate of the substance when water contacts the material 112. The increased quantity of the substance in the air indicates the present of a water leak near the device 100. Alternatively, the material 112 is designed to release a substance (scented or non-scented) into air, only when water 112 contacts the material. The presence of the substance in the air indicates the present of a water leak near the device 100.

The tray 102 is designed to be placed under a water pipe, and collect water from a leak, thereby preventing water from contacting, and potentially ruining, the surface under the pipe. For example, the tray 102 may designed to be placed on the bottom of a cabinet located under a sink. Optionally the tray 102 is made of a substance which is not ruined by contact with water, such as plastic. In an exemplary embodiment of the present invention, the internal length of the front wall 104 and the back wall 106 is about 28 inches, while the external length of the front wall 104 and back wall 106 is about 29 inches; the internal length of the left wall 108 and of the right wall 110 is about 16 inches, while the external length of the left wall 108 and the right wall 110 is 17 inches; and the depth of the tray 102 is about 1.5 inches.

Optionally, the material 112 includes a water soluble barrier covering a volatile substance. The water soluble barrier is designed to be dissolved upon contact with water. Optionally, the barrier limits the release into air of the substance, and the dissolving of the barrier causes an increase in the release rate of the substance in air. Alternatively, the barrier prevents the release into air of the material, and the dissolving of the barrier causes the volatile substance to be released into air. The water soluble barrier may be, for example, made of one or more water soluble polymers, such as polyvinyl alcohol, methyl cellulose, gelatin, or starch.

According to some embodiments of the present invention, the material 112 includes a chemical designed to react with water and release a product of the reaction as the released substance. The product may be a volatile substance, an aerosol, or a gas. In an exemplary embodiment, the material 112 includes a quantity of sulfur trioxide ($SO_3$), which reacts with water to provide sulfuric acid ($H_2SO_4$) aerosol, a substance that may be easily detected by a user's sense of smell, optionally along with other scented substances, such as essential oils. Included in the material 112.

The material 112 may be in many different forms, as will be shown below. In FIGS. 1a-1b, the material 112 is contained within a liner. The liner is designed to be removable and replaceable by a user. The material 112 contained in the liner releases the substance into air for a finite period of time, which will be hereafter referred to as the material's lifetime. The device 100 characterized by a removable and replaceable liner may be useful for detecting leaks even after the end of the material's lifetime. As the material's lifetime comes to an end, the device 100 may not be used to freshen air, until the liner is replaced. As the liner is replaced by a user, the user will check the tray for the presence of water, and if water is present, a leak will have been detected, even without a substance release.

Optionally, liners are provided in a variety of scents. A user may choose to replace a first liner characterized by a first scent, with a second liner characterized by a second scent. This may be useful, as the user may have grown accustomed to the first scent, and may no longer detect an intensifying of the first scent, as a consequence of a water leak. As the liners are replaced, the user may be more sensitive to an intensifying of the second scent, due to the water leak, and therefore may more quickly detect the water leak.

Optionally, the liner is flexible. In a variant, the liner is made of a absorbent material, such as a typical absorbent material used in most common paper air fresheners.

According to some embodiments of the present invention, a cabinet is provided, the bottom thereof is covered by a device, like the device 100.

FIG. 1b shows a view of the device 100 from the point of view of an observer located at a position 114 inside the device 100, and looking in the direction 116, toward the right wall 110.

Figure 2:
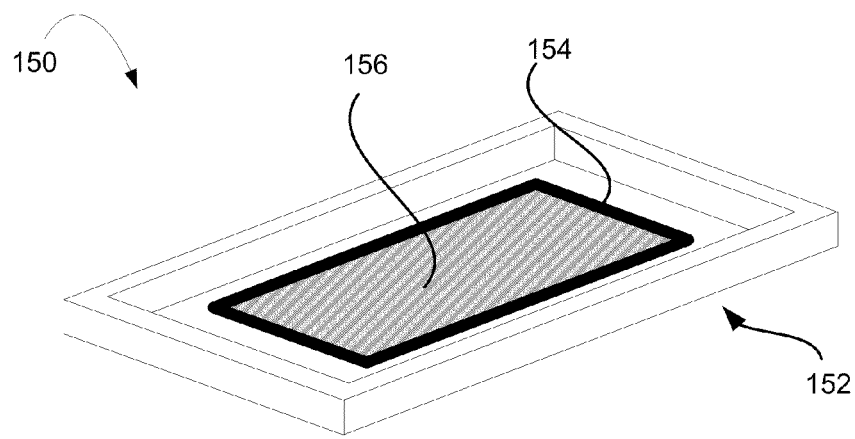
FIG. 2 is a schematic drawing representing a tray upon which is placed a cartridge containing a liner with an air freshening material, according to some embodiments of the present invention.

FIG. 2 is a schematic drawing representing a device 150, including a tray 152, upon which is placed a cartridge 154 containing a liner 156 with an air freshening material, according to some embodiments of the present invention.

The device 150 is similar to the device 100 of FIGS. 1a-1c. In the device 150, a flexible liner 156 is contained within a rigid cartridge 154. The rigid cartridge 154 facilitates the handling of the flexible liner 156. The flexible liner 156 may bend or crease while being slid into place, due to a force of friction between the liner 156 and the tray 152. The addition of the rigid cartridge 154 to the liner 156 prevents contact between the liner 156 and the tray, and therefore prevents any bending or creasing of the liner 156 due to friction between the tray 152 and the liner 156.

Figure 3:
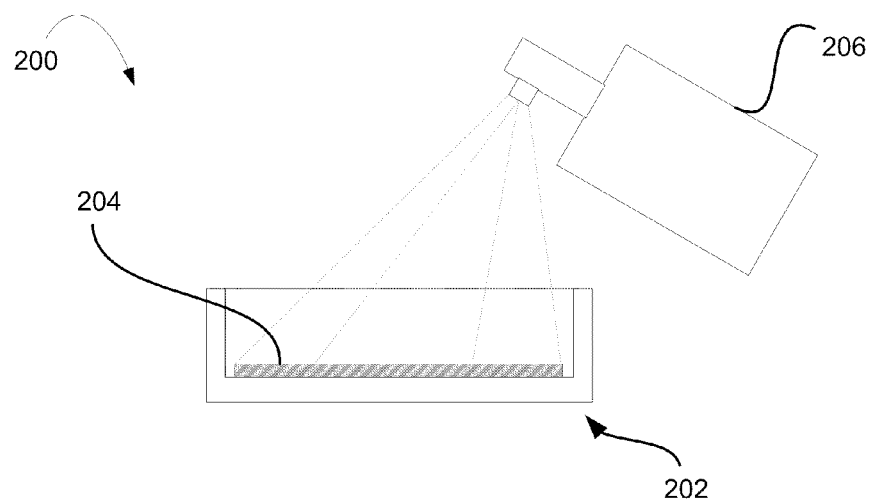
FIG. 3 is a schematic drawing illustrating a tray upon which the material is sprayed, such that a film of material forms upon the tray, according to some embodiments of the present invention.

FIG. 3 is a schematic drawing illustrating a device 200 including a tray 202 upon which a material 204 is sprayed, such that a film of material forms upon the tray 202, according to some embodiments of the present invention.

The device 200 includes a tray 202, and a film of material 204. The tray 202 is similar to the tray 102 of FIGS. 1a-1b. The material 204 is applied to the surface of the tray 202, by being sprayed from a container 206 upon the surface of the tray 202. Optionally, the material 204 is a solution which includes plastic microscopic spheres, onto which a water based or alcohol based scented liquid is applied. The solution is sprayed onto the tray 202, and left to dry. As the solution dries, a thin film forms around the spheres, slowing down the evaporation of the scented liquid, and therefore sealing in the scent. Wetting the material 204, dissolves the film around the spheres, and reactivates the scent. An exemplary material having such characteristics is NanoSal, developed by Salvona Technologies, Inc.

According to some embodiments of the present invention, the material 204 is sprayed upon a removable liner. When the effects of the material 204, the liner may be removed, sprayed upon again, and placed again upon the tray 202.

Figure 4:
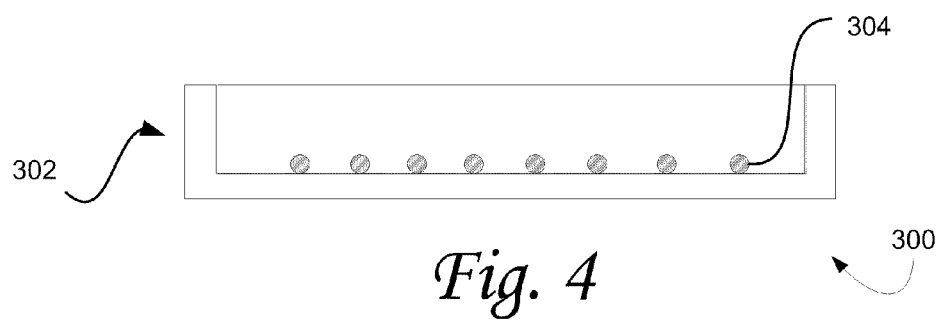
FIG. 4 is a schematic drawing, illustrating a tray upon which the material is placed in the form of granules or pellets, according to some embodiments of the present invention.

FIG. 4 is a schematic drawing, illustrating a device 300 including a tray 302 upon which a material is placed in the form of granules or pellets, according to some embodiments of the present invention.

The device 300 includes a tray 302, similar to the tray 102 of FIGS. 1a and 1b, and pellets or granules 304 of material, having the same properties of the material 112.

Figure 5A:
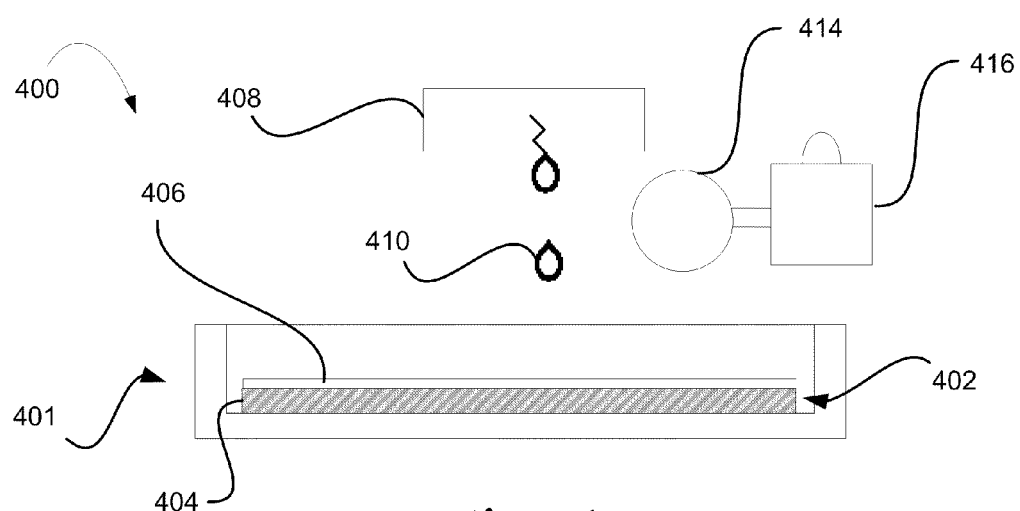
FIGS. 5a-5b are schematic drawings illustrating a material which includes a substance covered by a water soluble barrier, wherein the release of the substance in the air activates an alarm, according to some embodiments of the present invention.
Figure 5B:
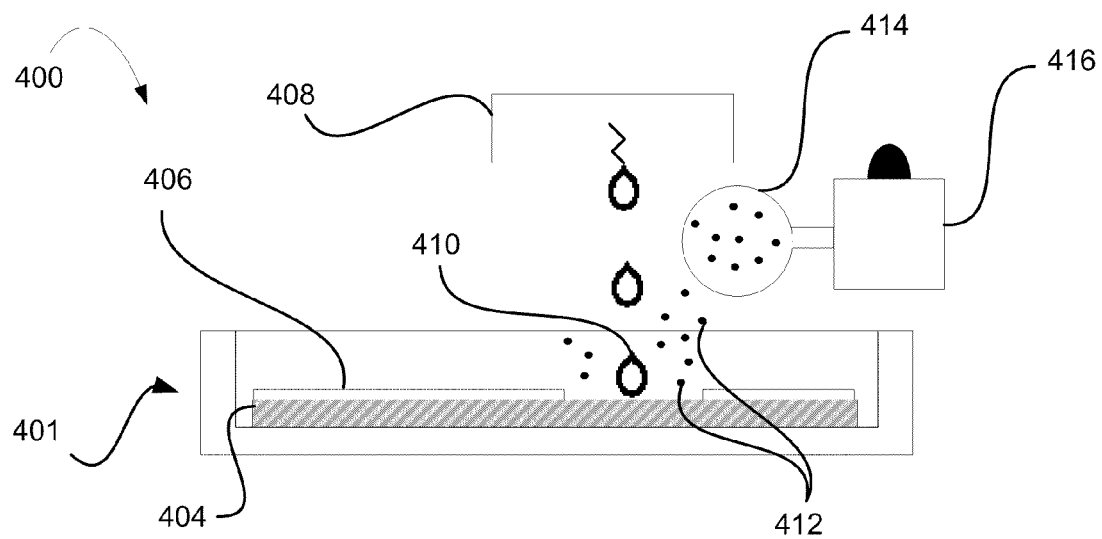

FIGS. 5a-5b are schematic drawings illustrating a device 400 including a material 402, which includes a substance 404 covered by a water soluble barrier 406, wherein the release of the substance 404 in air activates an alarm 416, according to some embodiments of the present invention.

The device 400 includes a tray 401, which contains a material 402. The tray 401 is similar to the tray 102 of FIGS. 1a-1b. The material 402 includes a substance 404, which may for example be a volatile substance or an aerosol, as described above. The substance 404 is covered by a water soluble barrier 406, as described above. The tray 401 is placed under a water pipe 408. The water pipe 408 has a leak, and a water drop 410 is part of the leak.

In FIG. 5b, the water drop 410 reaches and dissolves the barrier 406, and particles 412 of the substance 404 are released into air.

The particles are optionally, detected by a user through the user's sense of smell. Alternatively, the device 400 further includes a detector 414, which measures and monitors a density of the material 404 in air. The detector 414 is connected to an alarm 416. When the density of the material 404 in the air is higher than a predetermined density, the detector 414 activates the alarm 416, as shown in FIG. 4b.

The detector 404 may detect the presence of material in the air, through photoelectric, ionization, or air-sampling detection, or a combination thereof as is common is the art. The alarm 416 may produce a light, through LEDs or strobe lights, an audible tone, a spoken voice alert, as is common in the art.

Figure 6A:
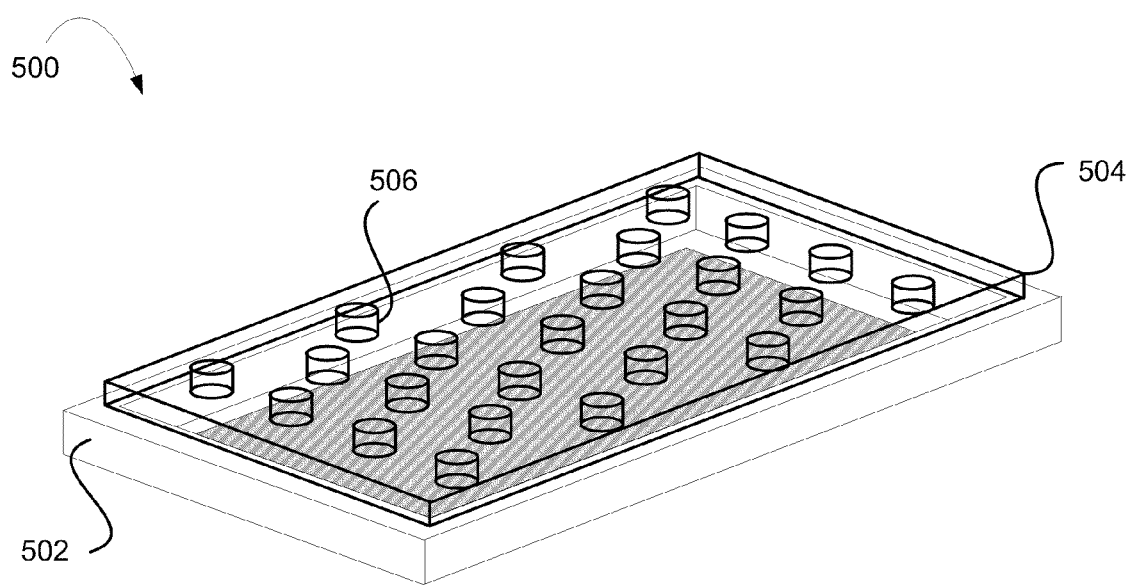
FIGS. 6a-6c are schematic drawings illustrating a tray holding a perforated panel, the panel being configured for supporting one or more items above the material, according to some embodiments of the present invention.
Figure 6B:
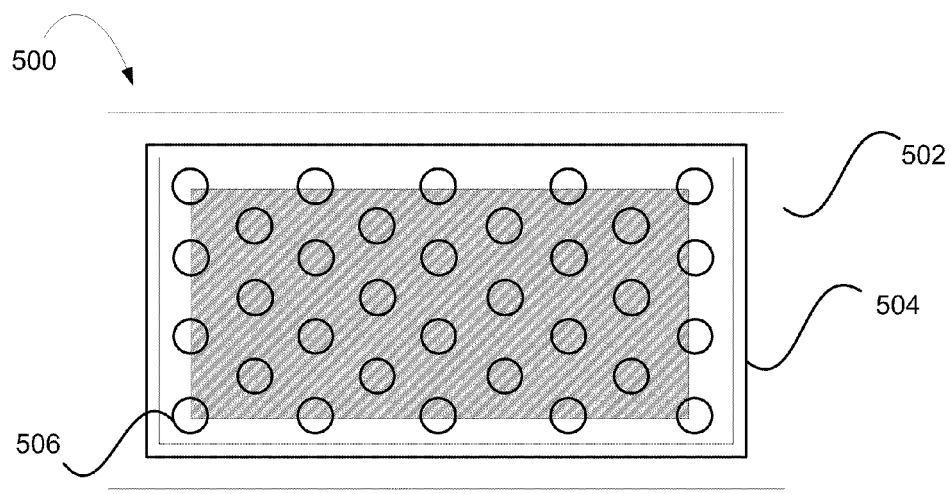
Figure 6C:
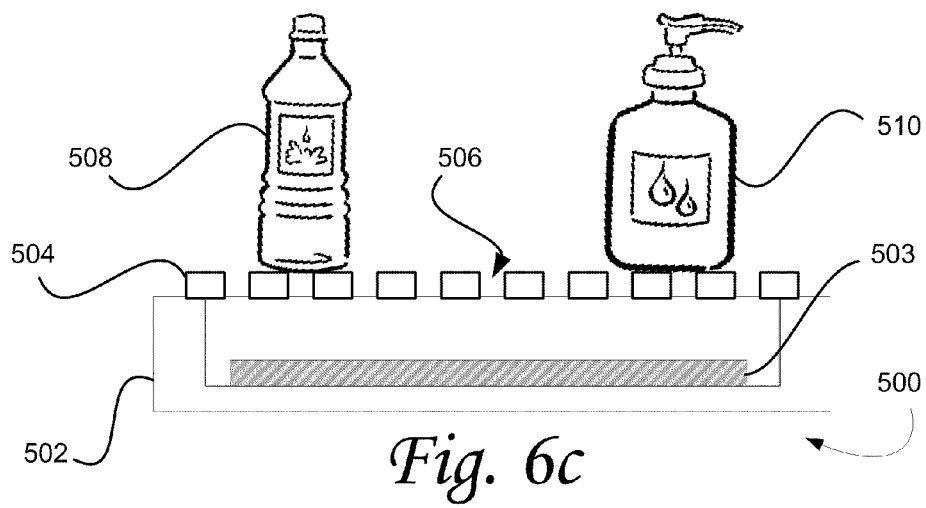

FIGS. 6a-6c are schematic drawings illustrating a device 500 including a tray 502, which holds an item supporting member 504, the member 504 being configured for supporting one or more items above the material, according to some embodiments of the present invention. The item supporting member is a perforated panel. FIG. 6a shows a perspective view of the device 500. FIG. 6b shows a top view of the device 500. FIG. 6c, show a side view of the device 500 from the inside of the device 500.

The device 500 includes a tray 502, similar to the tray 102 of FIGS. 1a-1b, containing a material 503, similar to the material 112 of FIGS. 1a-1b. The device 500 includes a panel 504 having holes, such as the hole 506. The panel 504 is held by the tray 502 and is designed to support one or more items, such as bottles 508 and 510. The holes on the panel allow water from a leak to reach the material 503, and the substance to be released into air.

The addition allows a user to more easily remove and/or replace the material 503. Without the panel, the items would be placed directly on the material 503, forcing the user to remove each item, for removing and/or replacing the material 503. The presence of the panel allows the user to lift the panel and items all at once, in order to reach the material 503.

Figure 7A:
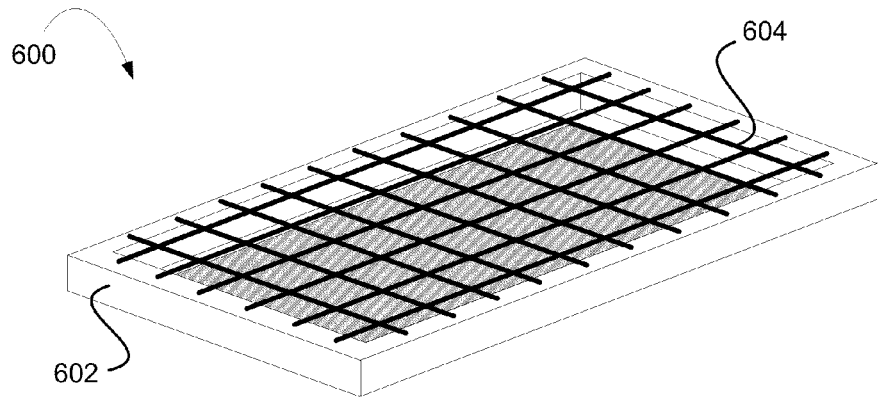
FIGS. 7a-7c are schematic drawings illustrating a tray holding a wire grid, the wire grid being configured for supporting one or more items above the material, according to some embodiments of the present invention.
Figure 7B:
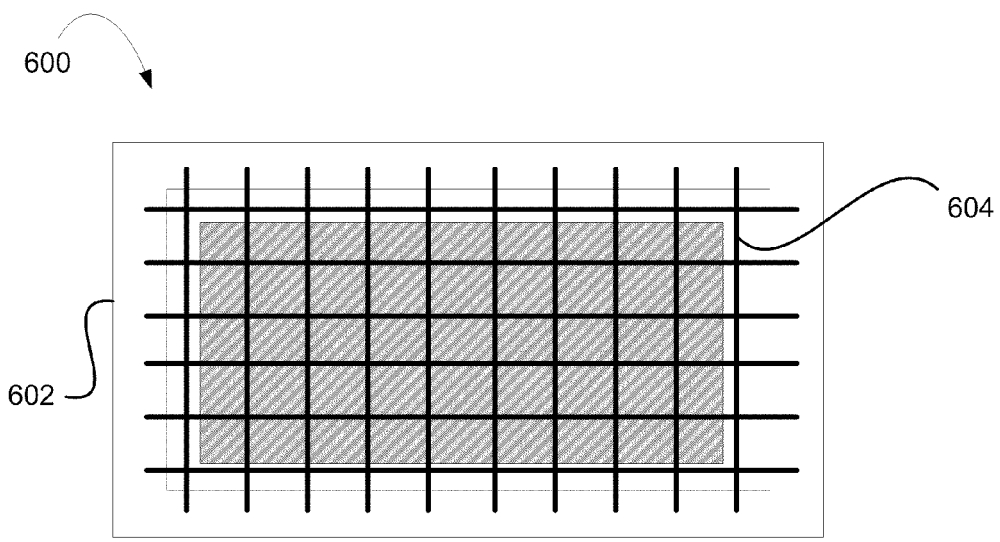
Figure 7C:
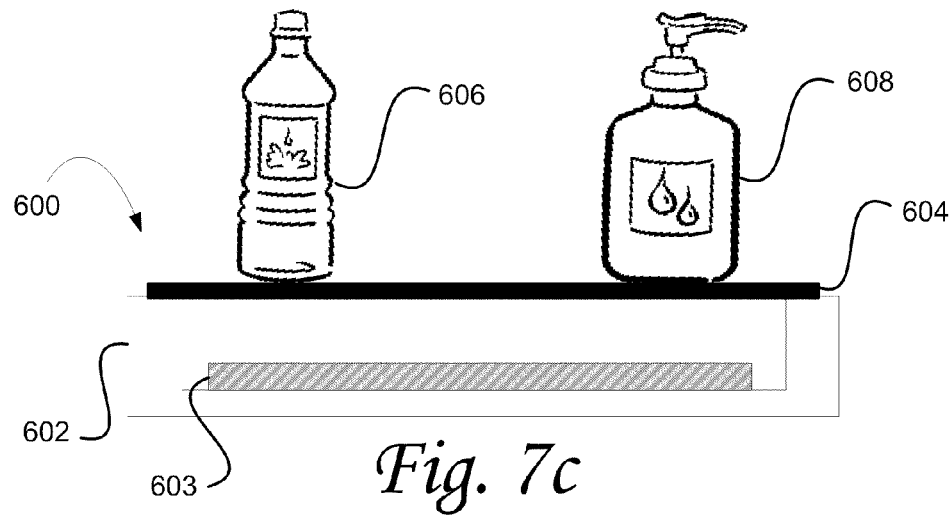

FIGS. 7a-7c are schematic drawings illustrating a device 600, including a tray 602 holding an item supporting member 604, the member 604 being configured for supporting one or more items above the material 603, according to some embodiments of the present invention. The item supporting member 604 is a wire grid. FIG. 7a shows a perspective view of the device 600. FIG. 7b shows a top view of the device 600. FIG. 7c, show a side view of the device 600 from the inside of the device 600.

The device 600 is very similar to the device 500 of FIGS. 6a-6c. Instead of the perforated panel, items, such as the bottles 606 and 608, are supported above the material 603, by the wire grid 604, which allows water from a leak to reach the material 503, and the substance to be released into air.

Figure 8A:
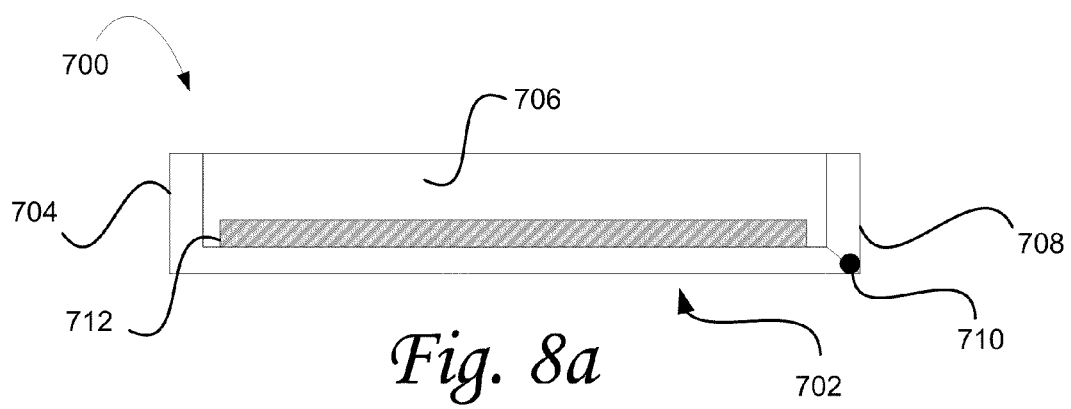
FIGS. 8a-8b are schematic drawings illustrating a tray characterized by a gate designed to be opened for easy access to the material, according to some embodiments of the present invention.
Figure 8B:
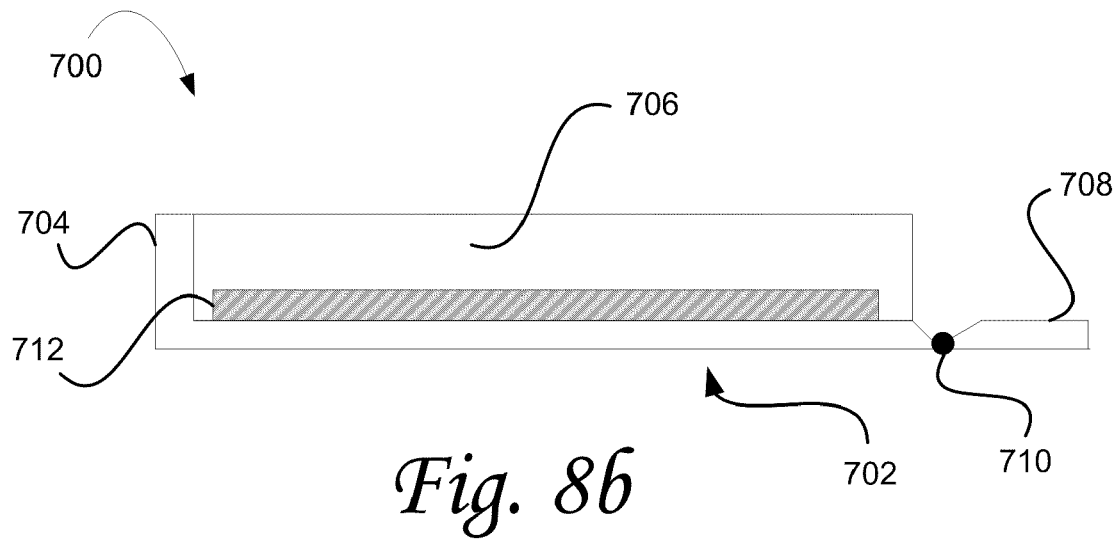

FIGS. 8a-8b are schematic drawings illustrating a device 700, including a tray 702 characterized by a gate 708 designed to be opened for easy access to the material 712, according to some embodiments of the present invention.

In FIGS. 8a-8b, the device 700 is viewed from a location inside the device 700. The tray 702 is similar to the tray 102 of FIGS. 1a-1b. However, the tray 702 is characterized by three walls and a gate. The back wall 704 and the right wall 706 are visible in the FIGS. 8a and 8b. The front wall includes or is replaced by a front gate 708, which is connected to the base of the tray 702 via a hinge 710. In FIG. 8a, the gate 708 is closed, to prevent water from leaving the tray 702. In FIG. 8b, the gate 708 is open, so that access to the material 712 is granted to a user, without the need to displace the tray 702.

If an item supporting member is present, such as the perforated panel 504 of FIGS. 6a-6c, or the wire grid 604 of FIGS. 7a-7c, the user may reach the material 712, without lifting or displacing the item supporting member and the items held by the item supporting member.

The device 700, with the addition of an item supporting member, as described above, may be used to cover the bottom of a cabinet, in order to protect the bottom of the cabinet from leaks, to detect leaks, and optionally, to give the cabinet a pleasant smell.

Figure 9:
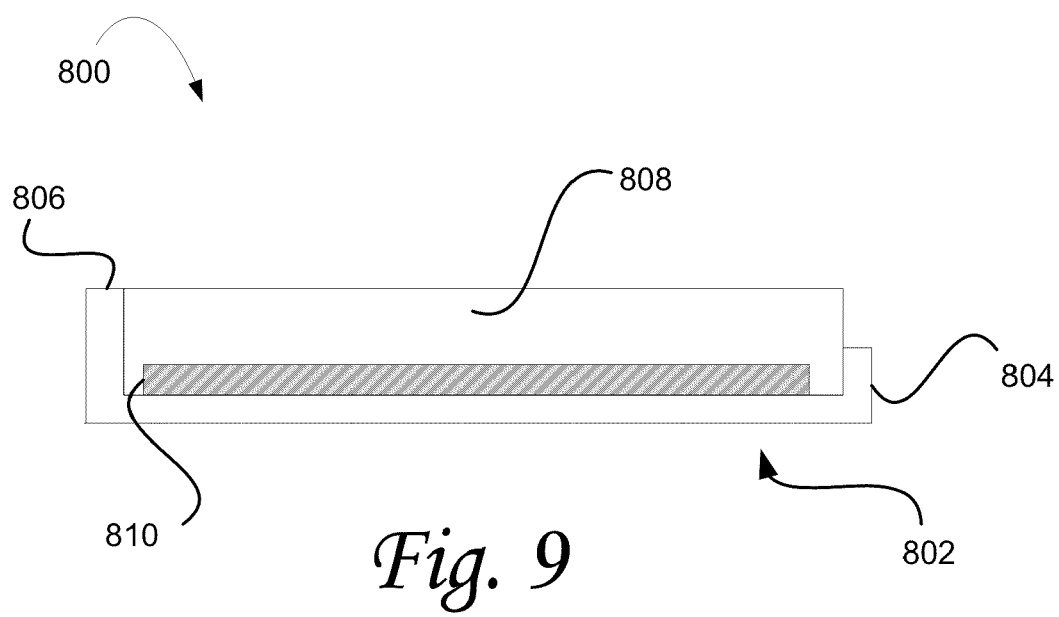
FIG. 9 is a schematic drawings illustrating a tray characterized by a low wall, designed for allowing easy access to the material, according to some embodiments of the present invention.

FIG. 9 is a schematic drawings illustrating a device 800 including a tray 802 characterized by a low wall, designed for allowing easy access to the material, according to some embodiments of the present invention.

The device 800 is viewed from a location inside the device 800. The tray 802 is similar to the tray 102 of FIGS. 1a-1b. However, the tray 802 is characterized by a low front wall 804. The back wall 806 and the right wall 808 are visible in FIG. 9. The low front wall 804 is designed to prevent water from leaving the tray 802, while allowing a user to access the material 810, without the need to displace the tray 802.

If an item supporting member is present, such as the perforated panel 504 of FIGS. 6a-6c, or the wire grid 604 of FIGS. 7a-7c, the user may reach the material 810 through the opening between the item supporting member and the high edge of the low wall 804, without lifting or displacing the item supporting member and the items held by the item supporting member.

The device 800, with the addition of an item supporting member, as described above, may be used to cover the bottom of a cabinet, in order to protect the bottom of the cabinet from leaks, to detect leaks, and optionally, to give the cabinet a pleasant smell.

Figure 10:
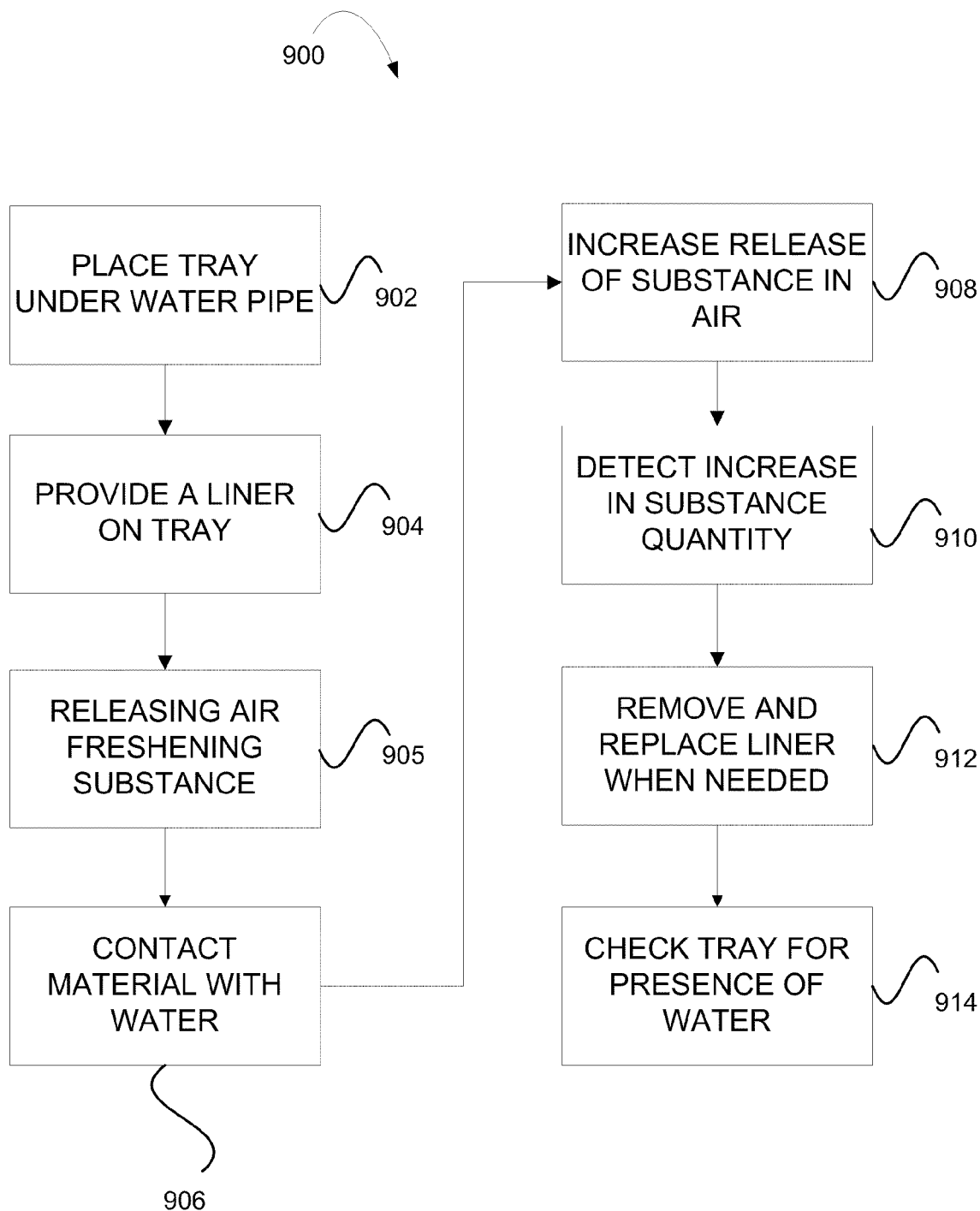
FIG. 10 is a flowchart illustrating a method for detecting water leaks and for protecting surface from water damage due to the leaks.

FIG. 10 is a flowchart illustrating a method 900 for freshening air, detecting water leaks, and protecting surface from water damage due to the leaks.

At 902, a tray is placed on a surface located under a water pipe, in order to collect water from a leak in the pipe, and protect the surface from water damage.

At 904, a liner containing a material is provided for being placed upon the tray. The material is designed to release an air freshening substance, and for increasing a rate of the release of the substance when the material comes into contact with water. Optionally, the material includes a water soluble barrier covering the substance, as explained above. Alternatively, the material is a chemical designed to chemically react with water, and a product of the reaction is the released substance, as explained above. The substance may be volatile, an aerosol, or a gas. The liner is designed to be removable and replaceable.

At 905, the air freshening substance is released in air.

At 906, the material contacts water. The tray ensures that water does not touch the surface.

At 908, the substance release rate is increased, as explained above.

At 910, the increased release of the substance is detected. Optionally, the substance is detected by a user through the user's sense of smell. Alternatively, the substance is detected by a detector, as explained above. In a variant, the detector monitors a density of the substance in the air, and activates an alarm, when the density of the substance is over a predetermined density, as explained above.

At 912, the liner is optionally removed and replaced, according to need. The removing and replacing may be performed at the end of the material's lifetime. The removing and replacing is achieved by the accessing by a user of the liner. Optionally, the liner is removed and replaced without a need to move the tray. For example, the material may be accessed through a gate or a low wall, as described below.

According to some embodiments of the present invention, a first liner is replaced by a second liner characterized by substance having a scent different than the scent of the substance included in the first liner. This may be useful, as the user may have grown accustomed to the first scent, and may no longer detect an intensifying of the first scent, as a consequence of a water leak. As the liners are replaced, the user may be more sensitive to an intensifying of the second scent, due to the water leak, and therefore may more quickly detect the water leak.

At 914, as the liner is being removed or replaced, the tray is checked for presence of water. This step allows a user to detect a leak, even after the end of the material's lifetime.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

The invention claimed is:

1. An air freshening device for detecting water leaks and protecting surfaces from water damage due to leaks, comprising:
   a tray, configured for being placed upon a surface located under a water pipe;
   a removable and replaceable liner placed upon the tray, the liner comprising a material configured for releasing an air freshening substance into air, and for increasing a release rate of the substance upon contact with water;
   wherein the increase of the release rate of the substance leads to an intensifying of a scent of the substance in air, and indicates the presence of a leak from the water pipe;
   and wherein the tray prevents water leaking from the water pipe from touching the surface;
   a detector, configured for monitoring a density of the substance in the air; and
   an alarm connected to the detector, and being configured for being activated by the detector, when the density of the substance increases above a predetermined density.

2. The device of claim 1, wherein the liner is flexible.

3. The device of claim 1, wherein the liner is at least partially enclosed in a rigid cartridge.

4. The device of claim 1, wherein the liner is available in different scents.

5. The device of claim 1, wherein the material comprises a water soluble barrier covering the substance and limiting the release of the substance, the water soluble barrier being configured for dissolving upon contact with water, thereby causing an increase of the rate at which the substance is released into air.

6. The device of claim 5, wherein the water soluble barrier comprises at least a water soluble polymer.

7. The device of claim 1, further comprising an item supporting member held by the tray above the liner, the member being configured for supporting at least one item, while allowing water to reach the liner.

8. The device of claim 7, wherein the item supporting member is one of:
   a perforated panel held by the tray above the material, the panel being configured for supporting at least one item, while allowing water to reach the material; and
   a grid of wires held by the tray above the material, the wire grid being configured for supporting at least one item, while allowing water to reach the material.

9. The device of any of claim 1, further comprising walls along the perimeter of the tray, such that at least one of the walls comprises a gate configured for being opened and closed, thereby allowing the liner to be replaced, without the need to remove the tray from the surface.

10. The device of claim 1, wherein the tray is configured for being inserted into a cabinet located under a sink, and wherein the surface is the bottom surface of the cabinet.

11. A cabinet, comprising the device of claim 1, the cabinet being configured for being located under a sink.

12. A device for detecting water leaks and protecting surfaces from water damage due to leaks, comprising:
   a tray, configured for being placed upon a surface located under a water pipe;
   a material placed upon the tray, the material being configured for releasing a substance into air upon contact with water;
   wherein the release of the substance indicates a presence of a leak from the water pipe, and the tray prevents water leaking from the water pipe from touching the surface;
   a detector, configured for monitoring a density of the substance in the air; and
   an alarm connected to the detector, and being configured for being activated by the detector, when the density of the substance increases above a predetermined density.

13. The device of claim 12, wherein the material is comprised in one of:
   a liner;
   a liquid configured for being sprayed upon the tray and, drying to form a film upon the tray; and
   a plurality of pellets or granules.

14. A method for freshening air, detecting water leaks, and protecting surfaces from water damage, comprising:
   placing a tray a upon a surface located under a water pipe, the tray being configured for preventing water leaking from the water pipe from touching the surface;
   providing a removable and replaceable liner placed onto the tray, the liner comprising a material being configured for releasing an air freshening substance into air, and for increasing a release rate of the substance upon contact with water;
   releasing the air freshening substance into air;
   contacting the material with water leaking from the water pipe;
   increasing the release rate of the substance the substance into air; and
   detecting an increased quantity of the substance in the air;
   using a detector for monitoring a density of the substance in air; and
   activating an alarm, if the density of the substance in air increases above a predetermined density.

15. The method of claim 14, further comprising:
   replacing the liner, when needed; and
   checking the tray for the presence of water.

16. The method of claim 15, wherein the replacing comprises replacing the liner with a liner configured for releasing a substance with a different scent.

17. The method of claim 14, wherein the material comprises a water soluble barrier covering the and limiting the release of the substance in air, the water soluble barrier being configured for dissolving upon contact with water, thereby causing an increase of the rate at which the substance is released into air.

18. The method of claim 14, wherein the detecting is performed through a user's sense of smell.

* * * * *